US010327930B2

(12) United States Patent
Li (10) Patent No.: US 10,327,930 B2
(45) Date of Patent: Jun. 25, 2019

(54) SYSTEM FOR IMPLANTING MEMBRANE, SYSTEM AND METHOD FOR IMPLANTING MEMBRANE AND STENT RESPECTIVELY

(71) Applicant: BEIJING ANGEL-REACH MEDICAL TECHNICAL CO., LTD., Beijing (CN)

(72) Inventor: Lei Li, Beijing (CN)

(73) Assignee: Beijing Angel-Reach Medical Technical Co., Ltd., Beijing (CN)

( * ) Notice: Subject to any disclaimer, the term of this patent is extended or adjusted under 35 U.S.C. 154(b) by 29 days.

(21) Appl. No.: 14/895,909

(22) PCT Filed: Aug. 13, 2014

(86) PCT No.: PCT/CN2014/084320
§ 371 (c)(1),
(2) Date: Dec. 3, 2015

(87) PCT Pub. No.: WO2015/196538
PCT Pub. Date: Dec. 30, 2015

(65) Prior Publication Data
US 2017/0105859 A1     Apr. 20, 2017

(30) Foreign Application Priority Data

Jun. 25, 2014   (CN) .......................... 2014 1 0293146

(51) Int. Cl.
*A61F 2/954*     (2013.01)
*A61F 2/966*     (2013.01)
(Continued)

(52) U.S. Cl.
CPC ................ *A61F 2/966* (2013.01); *A61F 2/07* (2013.01); *A61F 2/95* (2013.01); *A61F 2/954* (2013.01)

(58) Field of Classification Search
CPC .... A61F 2/95; A61F 2/954; A61F 2/97; A61F 2/966
(Continued)

(56) References Cited

U.S. PATENT DOCUMENTS 5,415,664 A * 5/1995 Pinchuk .................... A61F 2/95
                                                              604/523
5,571,172 A * 11/1996 Chin ......................... A61F 2/07
                                                              128/898
(Continued)

FOREIGN PATENT DOCUMENTS

CN          101045022 A          10/2007
CN          201578402 U           9/2010
(Continued)

OTHER PUBLICATIONS

European Patent Office, Extended European Search Report Issued in Application No. 14894193.3, dated Jul. 27, 2016, Germany, 8 pages.

(Continued)

*Primary Examiner* — Kathleen S Holwerda
(74) *Attorney, Agent, or Firm* — McCoy Russell LLP (57) ABSTRACT

The present invention discloses a system for implanting membrane, a system and method for implanting a membrane and a stent respectively. The system for implanting membrane comprising: a body guide wire, a guide core, movably sleeved on the body guide wire, and a catheter, for releasably holding a membrane, the catheter is movably sleeved outside of the guide core, wherein the system for implanting membrane is provided with an adjusting mechanism for adjusting the axial position of the membrane released by the catheter, and the adjusting mechanism is detachably connected with the membrane. The adjusting mechanism detachably connected with the membrane according to the present invention can not only adjust the axial position of the (Continued)

released membrane, but also causes no influence on the normal work of the blood vessel of a patient after the adjustment and improves the implanting efficiency and effect of the membranous stent.

3 Claims, 5 Drawing Sheets

(51) Int. Cl.
*A61F 2/07* (2013.01)
*A61F 2/95* (2013.01)

(58) Field of Classification Search
USPC .................. 623/1.11, 1.12, 1.23, 1.35
See application file for complete search history.

(56) References Cited

U.S. PATENT DOCUMENTS

| | | | | |
|---|---|---|---|---|
| 5,824,055 | A * | 10/1998 | Spiridigliozzi | A61F 2/954 |
| | | | | 623/1.11 |
| 6,669,707 | B1 * | 12/2003 | Swanstrom | A61B 17/0643 |
| | | | | 606/151 |
| 7,758,626 | B2 * | 7/2010 | Kim | A61F 2/07 |
| | | | | 606/108 |
| 7,763,063 | B2 | 7/2010 | Arbefeuille et al. | |
| 8,052,636 | B2 * | 11/2011 | Moll | A61B 34/71 |
| | | | | 600/114 |
| 8,491,612 | B2 * | 7/2013 | Stopek | A61B 17/11 |
| | | | | 606/153 |
| 2008/0051869 | A1 * | 2/2008 | Yribarren | A61F 2/954 |
| | | | | 623/1.11 |
| 2008/0269866 | A1 | 10/2008 | Hamer et al. | |
| 2009/0076592 | A1 | 3/2009 | Davidson et al. | |
| 2013/0338760 | A1 | 12/2013 | Aristizabal et al. | |

FOREIGN PATENT DOCUMENTS

| | | |
|---|---|---|
| CN | 101897629 A | 12/2010 |
| CN | 102488576 A | 6/2012 |
| CN | 103083122 A | 5/2013 |
| CN | 103126739 A | 6/2013 |
| CN | 203935299 U | 11/2014 |
| WO | 2009132309 A1 | 10/2009 |
| WO | 2013104324 A1 | 7/2013 |

OTHER PUBLICATIONS

State Intellectual Property Office of the People's Republic of China, Notice of Allowance Issued in Application No. 201410293146.X, dated Jun. 30, 2017, 3 pages.

European Patent Office, Notice of Allowance Issued in Application No. 14894193.3, dated Jul. 4, 2017, Netherlands, 5 pages.

* cited by examiner

SYSTEM FOR IMPLANTING MEMBRANE, SYSTEM AND METHOD FOR IMPLANTING MEMBRANE AND STENT RESPECTIVELY

CROSS REFFERENCE TO RELATED APPLICATIONS

The present application is a U.S. National Phase of International Patnet Application Ser. No. PCT/CN2014/084320, entitled "SYSTEM FOR IMPLANTING MEMBRANE, SYSTEM AND METHOD FOR IMPLANTING MEMBRANE AND STENT PESPECTIVELY," filed on Aug. 13, 2014, which claims priority to Chinese Patent Application No. 201410293146.X, entitled "SYSTEM FOR IMPLANTING MEMBRANE, SYSTEM AND METHOD FOR IMPLANTING MEMBRANE AND STENT RESPECTIVELY," filed on Jun. 25, 2014, the entire contents of each of which are hereby incorporated by reference for all purposes.

FIELD OF THE INVENTION

The present invention relates to the field of implanting membrane of membranous stent, and particularly, relates to a system for implanting membrane and a system and method for implanting membrane and stent respectively using said system.

BACKGROUND OF THE INVENTION

With the advent of an aging society, cardiovascular and cerebrovascular diseases are increasing. In the case of lesion of an aortic arch, blood flow needs to be isolated from the lesion portion to reduce the pressure on the vessel wall of the aortic arch. Wherein, the aortic arch is a segment of bent large vessel with multiple branches, the variations of three branches including the innominate artery, the left carotid artery and the left subclavian artery located on the aortic arch are relatively large, the diameters are different, the distances and angles with the aortic arch are different as well. Regarding them, a membranous stent is needed, a membrane thereof acts as an artificial vessel to guide the blood flow into the three branches, and the stent thereof plays a role of radially supporting and anchoring the membrane. In the prior art, the manner of implanting the membranous stent is to implant the membrane and the stent at the same time, namely, the membrane is coated on the stent in advance and is implanted in the vessel with the stent at the same time. However, there may be following problems in this manner:

1. The size of an implanting system for implanting the membranous stent must be too large to be conveyed in the vessel.
2. The body portion and the branch portions of the membrane are so difficult to position at the three-branch vessel that the implanting difficulty is high.
3. The endoleak rate in the membrane is relatively high, and the curative effect is poor.
4. Different membranes need to be customized for different patients, such that there is very long surgery waiting times and very high costs for the patients.

Therefore, there is positive significance in improving the membrane and the implanting system thereof, capable of solving at least one of the above-mentioned problems.

SUMMARY OF THE INVENTION

The purpose of the present invention is to provide a system for implanting a membrane and a system and a method for implanting the membrane and a stent respectively using the said system, and the system for implanting the membrane is capable of adjusting the axial position after the membrane is released.

To fulfill the above-mentioned purpose, according to one aspect of the present invention, a system for implanting membrane is provided. The system for implanting membrane, comprising: a body guide wire, a guide core, movably sleeved on the body guide wire, and a catheter, for releasably holding a membrane, the catheter is movably sleeved outside of the guide core, wherein the system for implanting membrane is provided with an adjusting mechanism for adjusting the axial position of the membrane released by the catheter, and the adjusting mechanism is detachably connected with the membrane.

Preferably, the membrane comprises a body portion, formed into a tubular structure, the adjusting mechanism comprises a front end control wire, detachably connected to the front end of the body portion, and a turn transmission structure, after being turned by which the front end control wire is extended backwards.

Preferably, the membrane comprises a body portion, formed into a tubular structure, the adjusting mechanism comprises a front end control wire, detachably connected to the front end of the body portion, and connected with the guide core.

Preferably, the catheter and the guide core are extended backwards respectively, the front end control wire after being set out from the front end of the body portion and turned by the turn transmission structure arranged on the guide core is passed through the guide core and is extended backwards.

Preferably, the turn transmission structure is formed into a turn hole structure for enabling the front end control wire to pass through.

Preferably, a guide head located in front of the body portion is fixed on the guide core, and is located in front of the catheter, and the turn transmission structure is arranged on the guide head forming a streamlined structure.

Preferably, the adjusting mechanism further comprises a back end control wire extended backwards is detachably connected to the back end of the body portion.

Preferably, the membrane comprises a body portion, formed into a tubular structure, and a branch portion, connected to the body portion, the system further comprises a branch guide wire, passed into the branch portion, the adjusting mechanism comprises a limiting knot, arranged on the branch guide wire, a limiting hole, located in front of the limiting knot and formed in the branch portion, and wherein the size of the limiting knot s larger than the limiting hole.

Preferably, wherein the limiting hole is formed by a limiting ring which is connected to the branch portion by a connecting wire and the limiting ring is spaced apart from the front end of the branch portion.

Preferably, a plurality of connecting wires are detachably connected to the branch portion along the circumferential direction uniformly.

Preferably, the limiting knot is detachably arranged on the branch guide wire.

Preferably, further comprises a guide core locking piece, for fixing the guide core relative to the catheter.

According to another aspect of the present invention, a system for implanting a membrane and a stent respectively is provided, the implanting system comprises said system for implanting membrane and a stent conveying device, for releasably holding and conveying a stent.

Preferably, the stent conveying device is sleeved on the guide core, the system further comprises a guide core locking piece, for fixing the guide core relative to the catheter, which is fixedly connected with the guide core and is provided with a first locking portion and a second locking portion, which are locked to the guide core in an unlockable manner respectively, and are spaced apart from each other along the axial direction of the guide core.

Preferably, the guide core locking piece has a first locking position and a second locking position. At the first locking position, the first locking portion is in an unlock condition, the guide core is locked by the second locking portion in front of the first locking portion, the stent conveying device sleeved on the guide core is slidden between the first locking portion and the second locking portion along the guide core. At the second locking position, the guide core is locked by the first locking portion, the second locking portion is in an unlock condition, and the stent conveying device is moved forwards through the second locking portion.

Preferably, the stent conveying device is sleeved on the guide core, the guide core comprises a guide wire hole, for enabling the body guide wire to pass through and a control wire hole, formed around the guide wire hole, which is formed on the side wall of the guide core and is extended along the same direction with the guide core. The outer wall of the guide core is formed into a noncircular section structure in profiled connection with the stent conveying device, and the noncircular section structure is provided with a convex form for forming the control wire hole.

Preferably, the system is used for implanting the membrane and the stent at a three-branch vessel of an aortic arch.

According to still another aspect of the present invention, a method for implanting a membrane and a stent respectively is provided. The method comprises a membrane implanting step and a stent implanting step, which carrying out in sequence. In the membrane implanting step: inserting a body guide wire into a blood vessel firstly, and moving a guide core movably sleeved on the body guide wire into the blood vessel therealong; then, movably sleeving a catheter releasably holding the membrane to the guide core and moving the catheter into the blood vessel along the guide core, adjusting the axial position of the membrane through an adjusting mechanism after the membrane is released by the catheter, and releasing the connection of the adjusting mechanism and the membrane, after the membrane is adjusted.

Preferably, when adjusting the axial position of the body portion of the membrane, the body portion is driven to move forward by a front end control wire, which is connected to the front end of the body portion, and turned backwards to extend outside the body.

Preferably, the body portion is driven to move backwards by a back end control wire, which is connected to the back end of the body portion and extends outside the body backwards.

Preferably, in the membrane implanting step: inserting a branch guide wire into a branch vessel of the blood vessel, movably sleeving the branch portion of the membrane on the branch guide wire, and when adjusting the axial position of the branch portion of the membrane, operating the branch guide wire to drive the branch portion to move forwards.

Preferably, in the stent implanting step, releasably holding the stent in a stent conveying device, and movably sleeving the stent conveying device on the guide core and being moved to the membrane along the guide core.

Preferably, in the course of the stent implanting step, the guide core is fixed relative to the catheter throughout.

By means of the above-mentioned technical solutions, the adjusting mechanism detachably connected with the membrane according to the present invention can adjust the axial position of the released membrane, without affecting vascular function of the patient.

Other features and advantages of the present invention will be illustrated in the following specific embodiments in detail.

BRIEF DESCRIPTION OF THE DRAWINGS

Accompanying drawings are used for providing further understanding of the present invention, constituting a portion of the description are used for explaining the present invention together with the following specific embodiments rather than limiting the present invention. In the accompanying drawings.

DETAILED DESCRIPTION OF THE EMBODIMENTS

A detailed illustration of the embodiment of the present invention will be given below in combination with the accompanying drawings. It should be understood that the embodiment described herein are merely used for illustrating and explaining the present invention, rather than limiting the present invention.

In the present invention, without instructions to the contrary, the used orientation words, such as "inside and outside" usually refer to inside and outside of a corresponding object contour, "far and near" refer to of the distance from a certain component to another component, and "front and back" are usually defined based on the implanting direction of a stent and related components along the vessel, namely, corresponding components enter the vessel forwards and withdraw from the vessel backwards. These orientation words are only used for explaining the present invention, rather than limiting the present invention.

To solve the problems in the prior art, a method for implanting membranous stent embodiment includes: at first, implanting a membrane, and then implanting a stent after accurately positioning the membrane, namely the method for implanting membrane includes a membrane implanting step and a stent implanting step which are carried out in sequence in order to implant the membrane and the stent respectively. Therefore both of the membrane and the stent can be accurately fitted on the three-branch vessel wall of an aortic arch. It should be noted that, the system and method for implanting membranous stent according to the present invention can also be applied to other positions of vessels needing membrane besides the three-branch vessel of the aortic arch, and the variations of the implanting position thereof shall fall within the scope of the present invention. Besides the implanting system, the present invention further improves the structures of the membrane and the stent themselves, and a detailed description of the present invention will be given below for four aspects, including membrane implanting, stent implanting, membrane structure, and stent structure.

[Membrane Implanting]

Figure 1:
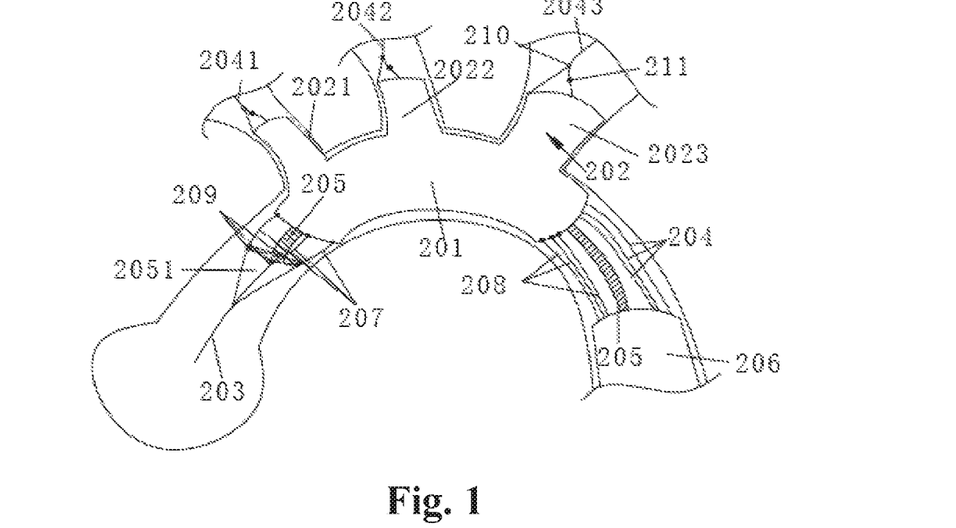
FIG. 1 is a schematic diagram of a structure of a system for implanting membranous stent according to one preferred embodiment of the present invention in course of implanting a membrane in a three-branch vessel of an aortic arch.
Figure 2:
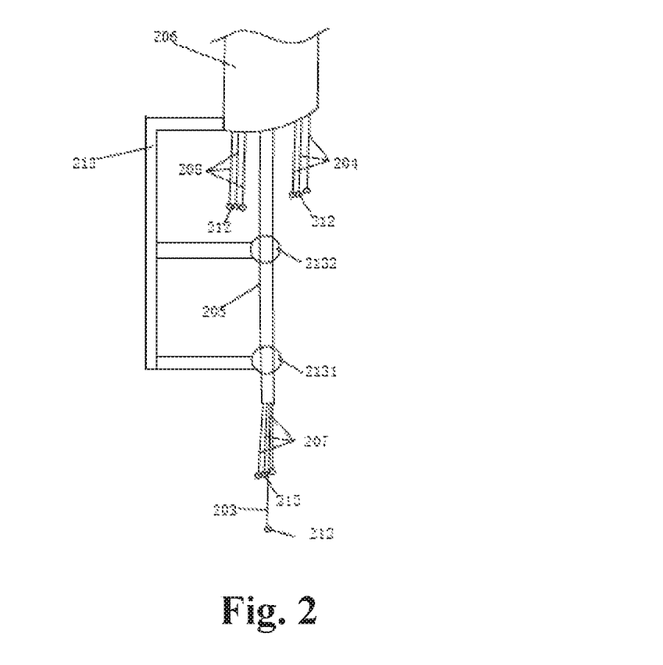
FIG. 2 is a schematic diagram of a structure of an operating portion in vitro of a system for implanting membranous stent according to one preferred embodiment of the present invention.
Figure 3:
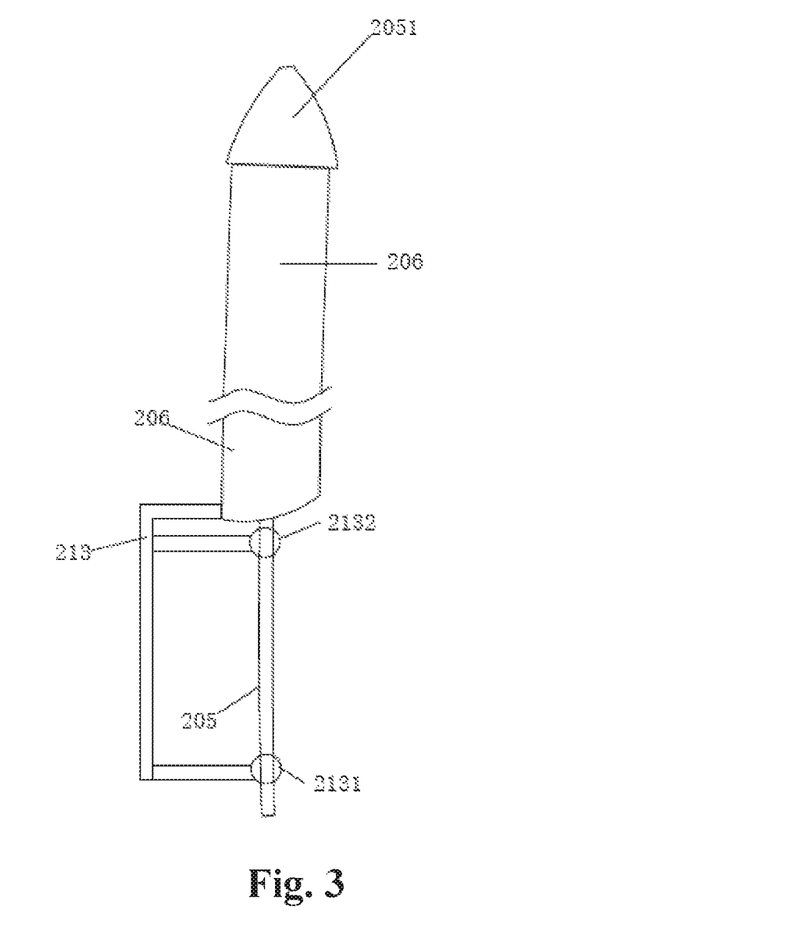
FIG. 3 is a schematic diagram of a structure of an external shape of a system for implanting membranous stent according to one preferred embodiment of the present invention.

At first, the system and method for implanting the membrane of the membranous stent will be illustrated below in combination with FIG. 1 to FIG. 3, wherein FIG. 1 schematically shows a structure of a portion in vivo of the system for implanting membrane according to the present invention, FIG. 2 schematically shows a structure of a portion in vitro of the system for implanting membrane according to the present invention, and FIG. 3 schematically shows an overall outline structure of the system for implanting membrane according to the present invention. In the system for implanting membrane according to the present invention, the membrane includes a body portion 201 formed into a tubular structure and branch portions 202 connected to the body portion 201, wherein the number of the branch portions 202 depends on the position of the used vessel. For example, at the position of the three-branch vessel of the aortic arch in the present invention, the branch portions include a first branch portion 2021, a second branch portion 2022 and a third branch portion 2023 to respectively adapt to the innominate artery, the left carotid artery and the left subclavian artery. Wherein, the method and system for implanting membrane according to the present invention may be capable of adjusting the axial position of the membrane at an end in vitro, including adjusting the axial positions of the front end and the back end of the body portion 201 and the front end of each branch portion 202. Specifically, at the one end in vitro, (for example at the back end), the axial position of the body portion 201 of the membrane ends is adjusted facing to the front and the back, and the axial position of the branch portion 202 of the membrane can also be adjusted through guide wires of the branch vessels so as to accurately fit the membrane with the vessel walls of the three branches. Further, the system for implanting membrane according to the present invention can also be used for keeping the invariable position of the positioned membrane in the subsequent stent implanting process to guarantee the accurate positioning of the entire membranous stent therefore.

Specifically, the membrane implanting step includes: at first, inserting a body guide wire 203 into a blood vessel, and moving a guide core 205 movably sleeved on the body guide wire 203 into the blood vessel along the body guide wire 203; then, movably sleeving a catheter 206 releasably holding the membrane to the guide core 205 and moving the catheter into the blood vessel along the guide core 205, adjusting the axial position of the membrane through an adjusting mechanism after the membrane is released by the catheter 206, and releasing the connection of the adjusting mechanism and the membrane, after the membrane is adjusted.

As shown in FIG. 1, the system for implanting membrane according to the present invention includes the body guide wire 203, branch guide wires 204, the guide core 205 and the catheter 206, wherein the guide core 205 is movably sleeved on the body guide wire 203, the catheter 206 holds the body portion 201 and the branch portions 202 of the membrane, and the catheter 206 is movably sleeved on the guide core 205. Wherein, the system for implanting membrane is provided with an adjusting mechanism for adjusting the axial position of the membrane released by the catheter 206, and the adjusting mechanism is detachably connected with the membrane. Therefore, after the membrane and the subsequent stent are implanted, the system for implanting membrane can be detached from the membrane to withdraw from the blood vessel.

More specifically, the body guide wire 203 is preferably a super-hard guide wire, which can be passed into the blood vessel from back to front to guide the subsequent components. Wherein, a guide head 2051 located in front of the body portion 201 is fixed on the guide core 205, the guide head 2051 is provided with a conical or other streamlined structure to guide the guide core 205 to nondestructively move along the blood vessel wall, the guide core 205 is of a hollow structure to be sleeved on the body guide wire 203 and move along the axial direction of the body guide wire 203, the number of the branch guide wires 204 depends on the number of branch vessels, and at the position of the three-branch vessel of the aortic arch in the present invention, the branch guide wires 204 include a first branch guide wire 2041, a second branch guide wire 2042 and a third branch guide wire 2043 to respectively correspond to the three branch vessels on the aorta. The catheter 206 is of a hollow structure to hold the compressed membrane, and the catheter 206 can be controlled by extending backwards to the end in vitro, for example, one handle located at the end in vitro. The catheter 206 is movably sleeved on the outer side of the guide core 205, which extends backwards as well, in order to both synchronously move with the guide core 205 under the control and move along the guide core 205. In addition, the front end of the catheter 206 has no connection relation with the guide head 2051, for example, the front end of the catheter can abut on the guide head 2051, and can also be positioned away from the guide head 2051 for a certain interval, in order to control the catheter 206 to withdraw from the membrane backwards to release the membrane when needing to release the membrane. At this time, the catheter 206 can be withdrawn from the membrane to release it only to serve as a channel for subsequent stent implanting therein.

Wherein, to accurately adjust and position the axial position of the body portion 201 after releasing the membrane, the adjusting mechanism according to the present invention includes a front end control wire 207 and a back end control wire 208, this two control wires are respectively connected to the front end and the back end of the body portion 201 of the membrane in various detachable manners known in the art, for example, an electrical detachment manner and mechanical detachment manner, wherein the electrical detachment manner can be achieved by applying current in vitro via related wires to fuse, and then release a connecting structure so as to separate corresponding portions. In addition, the number and connecting positions of the control wires are not limited, as long as the body portion 201 of the membrane can be stably pulled. For example, in a preferred embodiment of the present invention, three front end control wires 207 and three back end control wires 208 are arranged along the circumferential direction of the body portion 201 at equal intervals, in this way, the body portion 201 of the membrane can be stably pulled to move forwards or backwards. Wherein, it should be noted that to clearly display the back end control wires 208 and the branch guide wires 204 in FIG. 1, the three back end control wires 208 are not displayed as being arranged along the circumferential direction at equal intervals, which leads to no limitation to the present invention.

Specifically, when adjusting the axial direction of the body portion 201, the body portion moves forwards via the front end control wire 207, which is connected to the front end of the body portion, and turns backwards and extends in vitro. Wherein the body portion 201 is pulled and adjusted at the end in vitro towards the two ends, as a preferred embodiment, the adjusting structure in the present invention includes a turn transmission structure 209, and the turn transmission structure 209 can drive the corresponding control wire to turn. In one preferred embodiment according to the present invention, the front end control wire can extend backwards after being turned by the turn transmission structure 209, namely, the front end of the membrane can be pulled at the back end in vitro, and in combination with the back end control wire 208 extending backwards, the implanting system according to the present invention can be used for pulling towards the two ends of the membrane at the back end in vitro. Specifically, the turn transmission structure 209 is arranged in front of the body portion 201 of the membrane. It should be noted that in other embodiments, the manner of adjusting the front end of the membrane at the back end can also be connecting the front end control wire 207 with the guide core 205, specifically, the front end control wire can be directly connected to the guide core 205 or connected to the guide head 2051 to be indirectly connected with the guide core 205. In this way, when needing to adjust the front end of the membrane forwards, the guide core 205 only needs to be pushed forwards. In addition, in other embodiments, the manner of pulling the back end of the membrane is not limited to the manner of using the back end control wire 208, other manners can also be used, for example, no back end control wire 208 is arranged, and the back end of the membrane is pushed to cling to the blood vessel wall only by blood flow. Such variations shall fall within the scope of the present invention.

In one preferred embodiment of the present invention, specifically, the front end control wire 207 movably is passed through the guide core 205, and the turn transmission structure 209 is arranged on the guide core 205, preferably, arranged on the guide head 2051. Wherein, the turn transmission structure 209 can be a turn hole formed on the guide head 2051, and the turn hole is obtained by directly trepanning on the guide head 2051 and can be obtained by arranging a guide ring connected to the guide head 2051. In this case, the front end control wire 207 can pass into the guide core 205 after being led out from the front end of the body portion 201 and extend backwards along the guide core 205. Therefore, when needing to move the body portion 201 towards the front side, the front end control wire 207 only needs to be pulled at the back end in vitro to pull the body portion 201 forwards, and thus the entire structure is simple and ingenious.

In addition, the body portion 201 moves backwards through the back end control wire, which is connected to the back end of the body portion 201 and extends in vitro. Specifically, the back end control wire 208 can be directly connected to the back end of the body portion 201 in a detachable manner, being passed into the catheter 206 after being led out from the back end and extend backwards along the catheter 206. In this case, when needing to pull the body portion 201 backwards, the back end control wire 208 is directly pulled at the back end in vitro to drive the body portion 201 to move backwards. Therefore, the system and method for implanting according to the present invention can be used for accurately adjusting the axial position of the body portion 201 of the membrane at an end in vitro.

The adjustment of the axial position of the body portion 201 of the membrane has been described above, and the adjustment of the axial position of the branch portion 202 of the membrane will be described below. To this end, in the membrane implanting step, the branch portion 202 of the membrane is movably sleeved on the branch guide wire 204, it is the conception of the present invention, when the axial position of the branch portion of the membrane is adjusted, the branch guide wire 204 is operated to drive the branch portion 202 to move forwards. Specifically, due to the existence of the body portion 201, the implanting system only needs to pull the branch portion 202 forwards to fit the branch portion with the blood vessel wall without pulling the branch portion 202 backwards. Therefore, the branch guide wire 204 is innovatively adopted in the present invention to adjust the axial position of the branch portion 202, wherein the branch guide wire 204 is passed into the catheter 206 extending backwards to extend backwards along the catheter 206. Specifically, in order to adjust the branch portion 202 through the branch guide wire 204, the adjusting mechanism includes a limiting knot 211 arranged on the branch guide wire 204, and a limiting hole 210 is formed in the branch portion 202, wherein the size of the limiting knot 211 is larger than that of the limiting hole 210, and the limiting hole 210 is located in front of the limiting knot 211. Thus, when needing to pull the branch portion 202 forwards, the branch guide wire 204 only needs to be pulled forwards, and the limiting knot 211 will be clamped on the limiting hole 210 to drive the branch portion 202 to move forwards.

Wherein, the manner of forming the limiting knot 211 can be wound by two wires and can be connecting additional components on the wires. Wherein, preferably, the limiting knot 211 is detachably arranged in the branch guide wire 204, for example, two wires are wound at front and back ends in a detachable manner (electric detachment manner, mechanical detachment manner and the like). Whether the limiting knot 211 needs to be detached from the branch guide wire 204 depends on the final withdrawal manner of the branch guide wire 204, if the branch guide wire 204 is withdrawn from the front side, the limiting knot 211 needs to formed in a way that the limiting knot can be detached from the branch guide wire 204, if the branch guide wire 204 is withdrawn from the back side, the limiting knot 211 does not need to be detached from the branch guide wire 204, and the branch guide wire 204 is directly withdrawn from the back side.

In addition, the manner of forming the limiting hole 210 can be connecting a limiting ring to the branch portion 202, and the limiting ring can be formed by a metal capable of being implanted in human body. Due to a small size, the limiting ring can be retained in the patient body with the membrane without causing vasculopathy. In addition, in order not to affect the guide of the branch guide wire 204, the limiting ring is preferably connected with the branch portion 202 through a connecting wire to arrange the limiting ring and the branch portion at intervals, and thus the attrition of the branch portion 202 caused by the branch guide wire 204 can be reduced. To effectively pull the branch portion 202 of the membrane, a plurality of connecting wires are arranged and are uniformly and detachably connected with the branch portion 202 along the circumferential direction, thus the limiting ring is located at the radial center of the branch portion 202, for enabling the branch guide wire 204 to pull the branch portion 202 more effectively, at this time, the connecting wires can be detached from the branch portion 202, therefore after the detachment, the limiting ring can be withdrawn from the front side with the branch guide wire 204, and at this time, the limiting knot does not need to be detached. In this way, after the limiting ring is withdrawn, the blood flow in the blood vessel will not be interfered subsequently. Further, the limiting knot 211 and the limiting hole 210 also have other variations, and as long as not departing from the conception of the present invention, various variations shall fall within the scope of the present invention.

In addition, as shown in FIG. 1, since the back end control wire 208 and the branch guide wire 204 are passed into the catheter 206, for avoiding interference with the implanting of the stent subsequently, a guide wire holding groove extending along the extension direction of the catheter 206 can be formed on the inner wall of the catheter 206, such that corresponding wires only extend on the inner wall of the catheter 206 without affecting the subsequent implanting of the stent passed through the catheter 206.

The structure of a control end in vitro of the system for implanting membrane according to the present invention will be described below in combination with FIG. 2, wherein a control portion in vitro includes wire fixing pieces 212 for releasably fixing corresponding control wires and guide wires, and a guide core locking piece 213 for fixing the guide core 205 relative to the catheter 206, wherein the number of the wire fixing pieces 212 depends on the number of the guide wires and the control wires used in the present invention, the structure of each wire fixing piece is known to those skilled in the art, for example, a structure adopting a fixed plug, namely, corresponding wires are fixed on the fixed plug, when needing to fix the corresponding wires, the fixed plug only needs to be inserted into and fixed on such fixing matrixes as a handle and the like, and various variations of the wire fixing pieces 212 shall fall within the scope of the present invention. In addition, when the catheter 206 is withdrawn from the membrane and the membrane is controlled through the front end control wire 207, the position of the guide core 205 where the turn transmission structure 209 is located needs to be fixed, and preferably, the guide core locking piece 213 fixes the guide core 205 relative to the catheter 206. Wherein, the catheter 206 is fixed on base objects such as the handle and the like after extending to the end in vitro, thus the position of the guide core 205 can be fixed as well. The guide core locking piece 213 has a variety of embodiments, and the guide core locking piece 213 will be described below in detail in combination with the respective implanting of the membrane and the stent.

[Stent Implanting]

The implanting manner of the membrane according to the present invention has been described above, after the membrane is implanted, a stent needs to be implanted to support and anchor the membrane, namely, a stent implanting step will be carried out. The system for implanting the membrane and the stent respectively according to the present invention can include a stent conveying device 214 for releasably holding and conveying the stent, and the stent conveying device can be used for holding, conveying and releasing the stent by adopting various stent implanting manners in the art. In the stent implanting step according to the present invention, the stent is releasably held in the stent conveying device 214, and the stent conveying device 214 is movably sleeved on the guide core 205 and is moved to the membrane along the guide core 205. Namely, in the present invention, when subsequently implanting the stent, the guide core 205 in the system for implanting membrane is used as a guide wire for guiding the stent conveying device to move, that is, the stent conveying device 214 is movably sleeved on the guide core 205 and can move in the catheter 206 after the membrane is released, so that the respective implanting processes of the membrane and the stent can be organically combined to effectively implant the membranous stent.

In the present invention, when needing to use the guide core 205 to implant the stent, the relative position of the guide core 205 and the catheter 206 is always kept non-variable. That is, in the process of sleeving the stent conveying device 214 on the guide core 205 and moving along the guide core 205, the guide core 205 is always locked with the catheter 206 relatively. To this end, the guide core locking piece 213 according to the present invention adopts a special structure. Specifically, the guide core locking piece 213 is fixedly connected with the catheter 206 and is provided with a first locking portion 2131 and a second locking portion 2132, and the guide core 205 is locked by the first locking portion 2131 and the second locking portion 2132 respectively in an unlockable manner, which are arranged along the axial direction of the guide core 205 at intervals. Wherein, the guide core locking piece 213 can be fixedly connected with the catheter 206 in a direct fixed connection manner or in an indirect fixed connection manner, for example, both of the catheter 206 and the guide core locking piece 213 can be fixed on base objects such as an operating handle and the like, specifically, the back end of the catheter 206 is fixed on the operating handle, and the front end of the guide core locking piece 213 is fixed on the operating handle, such that the indirect fixed connection of the guide core locking piece 214 and the catheter 206 is achieved. Further, preferably, the back end of the guide core 205 is passed through the back end of the catheter 206, and the first locking portion 2131 and the second locking portion 2132 are respectively locked on the portion of the guide core 205 stretching out from the catheter 206 in an unlockable manner.

In a preferred embodiment of the present invention, the guide core locking piece 213 includes a rod-shaped body, which is fixedly connected with the catheter 206, the first locking portion 2131 and the second locking portion 2132 are respectively arranged on the rod-shaped body and are arranged along the length direction of the rod-shaped body at intervals, and the guide core 205 is locked by the two locking portions respectively in an unlockable manner, and which are arranged along the axial direction of the guide core 205 at intervals. Specifically, the first locking portion 2131 and the second locking portion 2132 extend from the rod-shaped body towards the guide core 205 along the same direction and are provided with locking structures for locking the guide core 205 in an unlockable manner at the end portions away from the rod-shaped body.

In addition, the locking structures of the two locking portions may be varied. In one preferred embodiment of the present invention, the locking structures are threaded locking pieces, threaded holes matched with the threaded locking pieces are correspondingly formed on the guide core 205, namely, the locking structures adopting bolt structures are inserted in or pulled out from the corresponding locking holes on the guide core 205, and various other locking manners known in the art shall fall within the scope of the present invention.

Wherein, in order to fix the guide core 205 relative to the catheter 206 in the stent implanting process, preferably, the guide core locking piece 213 includes a first locking position and a second locking position, the locking states of the first locking portion 2131 at the first locking position and the second locking position are opposite, and the locking states of the second locking portion 2132 at the first locking position and the second locking position are opposite. That is, when needing to implant the stent through the guide core 205, it is only needed to unlock the two locking portions in sequence and keep the locking states and the unlocking states of the two locking portions to be opposite. Specifically, at the first locking position, the first locking portion 2131 unlocks, the second locking portion 2132 in front of the first locking portion 2131 locks the guide core 205, and the stent conveying device sleeved on the guide core 205 is slidden between the first locking portion 2131 and the second locking portion 2132 along the guide core 205; at the second locking position, the first locking portion 2131 locks the guide core 205, the second locking portion 2132 unlocks, and the stent conveying device moves forwards to a preset position in the membrane through the second locking portion 2132. Wherein, when the stent conveying device mutually extending in vitro to be controlled is adopted, the distance between the first locking portion 2131 and the second locking portion 2132 needs to be guaranteed to be not smaller than the extension length of the stent conveying device, so as to avoid the stent conveying device from preventing the first locking portion 2131 from locking the guide core 205.

In this way, the stent can successfully pass through the two locking portions which are successively at the unlocking state in sequence, and the locking portions at the locking states can consistently keep the fixed relative position of the guide core 205 and the catheter 206, so that the position of the membrane is consistently kept to be invariable in the stent implanting process. Accordingly, in the method for implanting the membrane and the stent respectively, the stent can be accurately fitted on the three-branch vessel wall of the corresponding aortic arch together with the membrane after being implanted.

Figure 4:
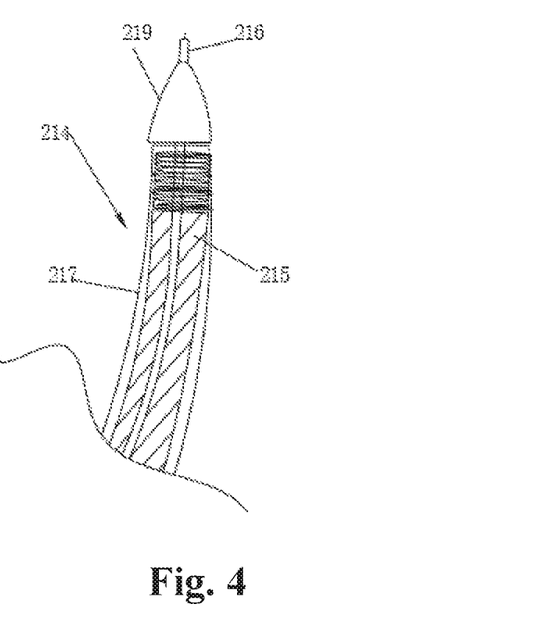
FIG. 4 is a schematic diagram of a structure of a stent conveying device according to one preferred embodiment of the present invention.

The implanting system for implanting the stent by passing through the membrane has a variety of forms, as long as the stent can be held and conveyed at a corresponding position inside of the membrane before being released. As an embodiment, as shown in FIG. 4, the stent conveying device 214 includes a stent catheter 217, a stent guide core 216 and a stent jacking core 215. Wherein, the stent is compressed and held in the stent catheter 217 and is sleeved on the stent guide core 216, the stent jacking core 215 is movably sleeved between the stent guide core 216 and the stent catheter 217 and is located at the back end of the stent, the stent guide core 215, the stent catheter 217 and the stent jacking core 216 can respectively extend backwards to the end in vitro to be controlled, and a stent guide head 219 of a streamlined structure is fixed at the front end of the stent guide core 215. Therefore, when implanting the stent, the stent guide core 216 is slidably sleeved on the guide core 205, so that the stent conveying device 214 enters the catheter 206 and moves forwards, and the stent catheter 217, the stent guide core 216 and the stent jacking core 215 are operated to implant the stent in a corresponding position along the guide core 205. After the stent is conveyed to the corresponding position, the stent jacking core 215 is fixed, then the stent catheter 217 is withdrawn backwards, and thus the stent is unfolded and is fitted on the membrane. Finally, the stent jacking core 215, the stent guide core 216 and the stent catheter 217 are withdrawn backwards to complete the implanting of the stent. It should be noted that the extension lengths of the stent catheter 217, the stent guide core 216 and the stent jacking core 215 included in the above stent implanting device are not larger than the distance between the first locking portion 2131 and the second locking portion 2132, so as not to affect the normal work of the guide core locking piece 213.

Figure 5:
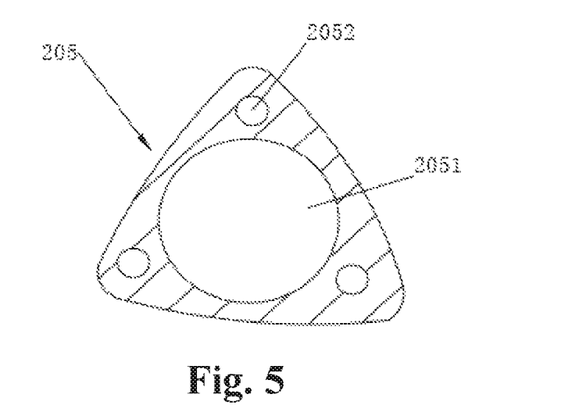
FIG. 5 is a schematic diagram of a sectional structure of a guide core according to one preferred embodiment of the present invention.

Further, considering that the front end control wire 207 needs to movably pass through the guide core 205 and the stent needs to be implanted along the guide core 205, thus the guide core 205 is further improved in the present invention. Specifically, as shown in FIG. 5, the guide core 205 includes a guide wire hole 2051 for enabling the body guide wire 203 to pass through and a plurality of control wire holes 2052 formed around the guide wire hole 2051, wherein the control wire holes 2052 are formed on the side wall of the guide core 205 and extend in the same direction as the guide core 205. More preferably, the outer wall of the guide core 205 is formed into a noncircular section structure, and the noncircular section structure is provided with a convex form for controlling the control wire holes 2052. For example, a triangular structure as shown in FIG. 5 is adopted, but it is not limited hereto. Therefore, the projection of this noncircular section structure can not only be used for forming the control wire holes 2052 to hold such control wires as the front end control wire 207 and the like, moreover, as long as the inner wall of the stent guide core 216 in the stent conveying device 214 is designed to be matched with the shape of the outer wall of the guide core 205, a profiled connection relation can be established between the guide core 205 and the stent guide core 216 to simultaneously rotate the stent conveying device 214 by rotating the guide core 205 to adjust the circumferential direction of the stent, and in this way, the positioning precision of the stent can be better guaranteed.

When the membrane and the stent of the above-mentioned membranous stent are accurately positioned, the guide core 205, the catheter 206, various wires, and the stent conveying device of the system for implanting membrane can be withdrawn backwards from the human blood vessel to complete the implanting of the membranous stent according to the present invention. It should be noted that, in the method for implanting membranous stent according to the present invention, the stent can also be implanted by adopting other stent implanting technology known in the art, and the stent can also be implanted subsequently by adopting the implanting manner of the branch vessel disclosed in FIG. 1 in the present invention, and various variations of the stent implanting shall fall within the scope of the present invention.

[Membrane Structure]

The system and method for implanting the membranous stent according to the present invention have been described above. Wherein, to adapt to various shapes, sizes and angles of the three branches of the aortic arch, successful improvement is made on the membrane itself in the present invention, which is capable of expansion and shrinkage in various directions. It is achieved that different membranes do not need to be customized according to the features of individual vessels.

Figure 6:
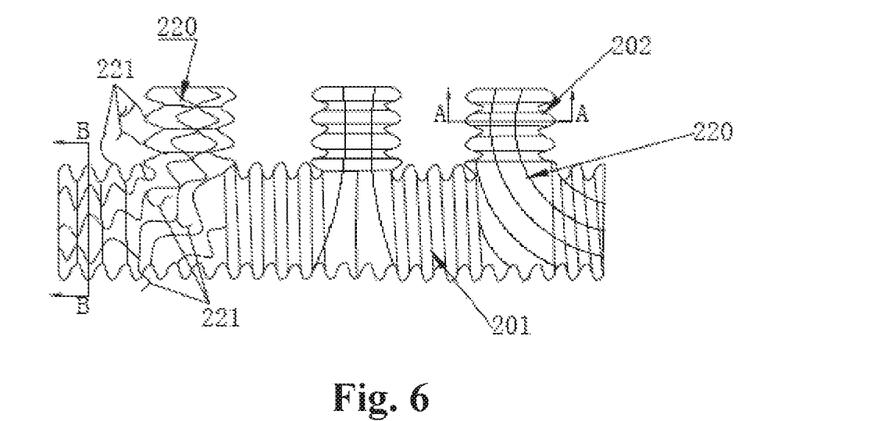
FIG. 6 is a schematic diagram of a structure of a membrane according to one preferred embodiment of the present invention.
Figure 7:
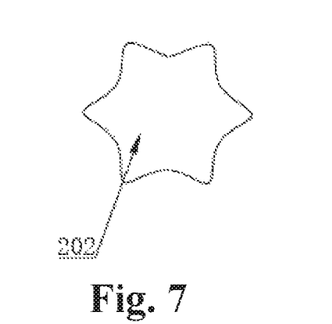
FIG. 7 is a schematic diagram of a sectional structure taken along a line A-A in FIG. 6.
Figure 8:
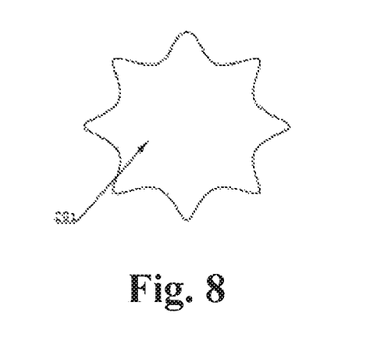
FIG. 8 is a schematic diagram of a sectional structure taken along a line B-B in FIG. 6.

As shown in FIGS. 6-8, the present invention further provides a membrane of a membranous stent. The membrane body of the membrane includes a body portion 201 and branch portions 202 connected to the body portion 201 and communicated therewith, wherein to fulfill the purpose of the present invention, as shown in FIG. 6. The body portion 201 is at least partially formed into a first ripple structure capable of being compressed along the axial direction thereof, an arc corrugation 220 is further formed on the membrane, which is extended from each branch portion 202 to the body portion 201. Moreover, as shown in FIG. 7, and FIG. 8, the arc corrugation 220 is constructed as a second ripple structure capable of compressing the body portion 201 and the branch portion 202 vertical to extension direction of the arc corrugation 220 respectively.

Wherein, it should be noted that to clearly illustrate the structure in the present invention, the arc corrugation 220 is drawn in two different manners in FIG. 6, specifically, the arc corrugation in the left side of the body portion 201 is drawn in a manner of indicating the ripple structure thereof and the arc corrugations 220 of other portions are simply drawn to indicate the extension directions thereof, by means of the comparative drawing method, it can be clearly displayed that the body portion 201 and the branch portion 202 are formed into the ripple structures which are compressed along the extension directions of the arc corrugations 220. For example, the end portion of the body portion 201 can be compressed along the axial direction through the first ripple structure, and the end portion can be compressed along the radial direction due to the arc corrugation 220. Therefore, the body portion having the first ripple structure and the second ripple structure of the membrane according to the present invention can be randomly varied in the axial direction and the radial direction. Moreover, according to the properties of the ripple structures, the body portion forming the first ripple structure can also be bent in the axial direction, thereby being capable of completely adapting to the variation in shapes, sizes, and angles of blood vessel walls of the main blood vessels and in the various branch vessels.

Preferably, the branch portion 202 is formed into a third ripple structure, which can be compressed along the axial direction. Therefore, the membrane according to the present invention can also adapt to the variations on the angles and sizes of the blood vessel walls of auxiliary blood vessels in the branch vessels.

Preferably, as shown in FIG. 6, to optimize the overall structure, the body portion 201 between the end portion of the body portion 201 and the branch portion 202 is formed into the first ripple structure. More preferably, under the condition of a plurality of branch portions 202, the body portion 201 between the adjacent branch portions 202 is respectively formed into the first ripple structures. In the application field of the present invention in the three-branch vessel of the aortic arch, three branch portions are arranged. By means of this reasonable design, under the condition of keeping the random variation of the body portion 201, the structure is simpler and the processing is convenient.

In addition, the membrane according to the present invention further includes a plurality of tightening wires 221 arranged on the first ripple structure and/or the second ripple structure and/or the third ripple structure, and each tightening wire 221 is fixed on the wave crest of the first ripple structure and/or the second ripple structure respectively.

Therefore, when needing to compress the corresponding ripple structure on the membrane, the tightening wire 221 on the wave crest of the corresponding position only needs to be tightened and bundled, such that the tightening wires 221 arranged on different positions can be used for changing the size of the membrane in the axial direction and the radial direction. The inside diameters and the lengths of the body portion 201 and the branch portions 202, the inclination angles of the branch portions 202 relative to the body portion 201, the distance between the branch portions 202 and the like can be adjusted.

Wherein, more preferably, the tightening wire 221 is fixed on the wave crest at the corner position of the arc corrugation 220, namely formed on the second ripple structure, wherein the corner position is the corner position (see the tightening wire 221 marked at the lower side in FIG. 6) in the extension direction of the arc corrugation 220, and the specific position thereof is at a position aligned with the branch portions 202 on the body portion 201. Therefore, the tightening wire 221 can not only be used for tightening leftwards to control the length of the body portion and tightening up or down to control the diameter of the body portion, but also can be used for tightening rightwards to control the distance between the branch portions 202 and is tightened up with the tightening wires of the branch portions 202 to control the inclination angles of the branch portions 202. The tightening portion on the corner position can be tightened with the tightening wires 221 in any direction on the surrounding thereof, and thus the diameter and the length of the body portion 201 of the membrane and the angles of the branch portions 202 can be adjusted by the tightening wire 221 at the corner.

Therefore, the membrane according to the present invention can be processed according to the properties of the blood vessels of patients in vitro for the second time, such that the membrane can better adapt to the blood vessels of different people, and different membranes do not need to be customized for different people, so that the cost is lower and the practicability is better.

Wherein, the specifications of the ripple structures on the membrane according to the present invention depend on the shapes of the used blood vessels, in addition, the membrane according to the present invention can be hot pressed by such high polymer materials capable of being implanted in human body as PTFE and the like, and various variations of the size, specification and material and the like of the membrane shall fall within the scope of the present invention.

[Stent Structure]

Besides the membrane, improvement is made on the stent in the membranous stent in the present invention. Wherein, due to the existence of the branch portion 202 of the membrane, if the stent for supporting and anchoring the membrane adopts an overall structure, hole resistance is generated on the branch portion to affect the blood flow of the branch portion. Therefore, in the prior art, a single stent is respectively implanted at both ends of the membrane, in this way, the membrane can be supported and anchored, and the smooth blood flow of the branch portion can be kept. However, the implanting process of the stent is difficult.

Figure 9:
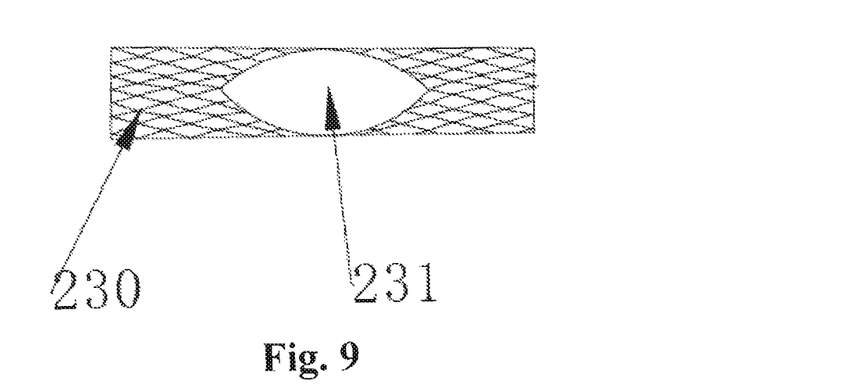
FIG. 9 is a schematic top view of a structure of a stent according to one preferred embodiment of the present invention.
Figure 10:
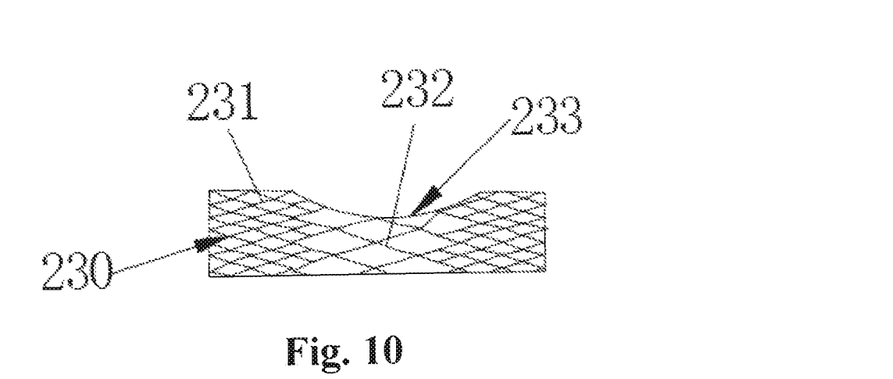
FIG. 10 is a schematic side view of a structure of a stent according to one preferred embodiment of the present invention.

To solve this problem, an overall stent is adopted in the present invention, however the hole resistance problem of the branch portion can be effectively avoided. Specifically, as shown in FIG. 9 and FIG. 10, the stent according to the present invention includes a stent body 230, and a notch portion 233 corresponding to the branch portion 202 of the membrane is formed on the stent body 230. Therefore, due to the existence of the notch portion 233, no hole resistance is generated on the branch portion 202 of the membrane, and the membrane is supported and anchored by one overall stent. It should be noted that this feature is not obvious, but this type of stents can be used because the branch portion 202 is on one side of the body portion 210 and the implanting system according to the present invention can keep positioning of the stent in the circumferential direction, where the notch portion 233 corresponds to the branch portion 202. Otherwise, if positioning of the stent in the circumferential direction cannot be kept, this stent with the notch portion 233 will not be used.

In the present invention, to keep positioning of the stent in the circumferential direction, the branch guide wire can be passed into the notch portion 233, in this case, the circumferential direction of the notch portion 233 can be basically determined to correspond to the branch portion 202, and after the stent enters the membrane, the guide core can be rotated to rotate the stent by means of the particular guide core rotation manner in the present invention, so as to keep the notch portion 233 to completely correspond to the branch portion 202. Wherein, the notch portion 233 can be designed according to the size and number of the branch portions 202, and the variations of the size and number of the notch portions 233 shall fall within the scope of the present invention.

Further, the stent body 230 includes dense portions 231 located at both ends and a loose portion 232 between the dense portions, wherein the framework density of the dense portions 231 is larger than the framework density of the loose portion 232, and the notch portion 233 is formed on the loose portion 232. In this way, even if the notch portion 233 cannot accurately correspond to the branch portion 202, the loose portion 232 can effectively avoid the hole resistance of the branch portion 202 due to the small framework density. Wherein, the framework density mentioned in this paper refers to the density of wires (for example, metal wires) designed at corresponding positions during manufacturing of the stent. In this way, the dense portions 231 located at both ends can play a radial supporting role on the stent body 230, while the loose portion 232 at the middle can prevent the hole resistance of denser wires on the blood vessel more reliably to better facilitate the normal work of the human blood vessel. In a preferred embodiment of the present invention, the framework density of the dense portions 231 located at both ends is the same.

In addition, as shown in FIG. 9 and FIG. 10, in a preferred embodiment of the present invention, the stent body 230 is formed into a straight tubular structure and is composed of two dense portions 231 and one loose portion 232. Wherein, the length ratio of each dense portion 231 to the loose portion 232 is 1:3 to 1:2, to better support the blood vessel in the radial direction. In one embodiment, preferably, the framework density of the loose portion 232 is uniformly distributed along the axial direction, and the ratio of the density of the loose portion 232 to the framework density of the dense portions 231 is 1:10 to 1:2. In another embodiment, preferably, the framework density of the loose portion 232 is not uniformly distributed, but the framework density gradually increases from the axial center to the two ends. Therefore, the stent according to the present invention better supports the blood vessel, has a good effect and effectively solves the hole resistance problem.

In addition, the stent body 230 can be woven by such wire materials as metal tantalum, medical stainless steel and nickel-titanium alloy and the like to form a Z-shaped compressible structure, and various variations of the material and the compression structure of the stent body known in the art shall fall within the scope of the present invention. In addition, to correspond to the three branch vessels of the three-branch vessel of the aorta, one notch portion 233 can be formed and correspond to the three branch vessels at the same time, or a plurality of notch portions can be formed and respectively correspond to different branch vessels, and such variations shall fall within the scope of the present invention.

To sum up, the system and method for implanting membranous stent applied to the three-branch vessel of the aortic arch and the used membrane and stent are emphasized in the present invention, so that the membrane and the stent can be accurately positioned, the structure is simple, the operation is simple, and the practicability and the promotional value are high.

The preferred embodiments of the present invention have been described above in detail in combination with the accompanying drawings. However, the present invention is not limited to the specific details in the above-mentioned embodiments. A variety of simple variations can be made to the technical solutions of the present invention within the scope of the technical conception of the present invention, and these simple variations belong to the scope of the present invention.

In addition, it should be noted that, various specific technical features described in the above specific embodiments can be combined in any proper manner under the condition of generating no contradiction, and to avoid unnecessary repetition, a variety of possible combinations will not be additionally illustrated in the present invention.

Further, various different embodiments of the present invention can be randomly combined, as long as not deviating from the thought of the present invention, and the combinations should be regarded as contents disclosed by the present invention.

The invention claimed is:

1. A system for implanting a membrane and a stent respectively, wherein the implanting system comprises:
   a body guide wire;
   a guide core, movably sleeved on the body guide wire;
   a catheter, for releasably holding a membrane, the catheter movably sleeved outside of the guide core;
   wherein the system for implanting the membrane is provided with an adjusting mechanism for adjusting an axial position of the membrane released by the catheter and the adjusting mechanism is detachably connected with the membrane,
   wherein the membrane comprises a body portion, formed into a tubular structure, and at least one branch portion, connected to the body portion, a branch guide wire passed into the branch portion,
   wherein the adjusting mechanism comprises a limiting knot arranged on the branch guide wire, and a limiting hole located in front of the limiting knot and formed in the branch portion, a size of the limiting knot larger than a size of the limiting hole; and
   a stent conveying device for releasably holding and conveying the stent,
   wherein the adjusting mechanism further comprises:
   a front end control wire, detachably connected to a front end of the body portion, and
   a turn transmission structure, turning the front end control wire that is extended backwards after a turn, wherein the turn transmission structure is a turn hole formed on a guide head;
   wherein the catheter and the guide core are extended backwards respectively, and the front end control wire, after being set out from the front end of the body portion and turned by the turn transmission structure arranged on the guide core, is passed through the guide core and is extended backwards;

wherein the stent conveying device is sleeved on the guide core, the system further comprising:

a guide core locking piece, for fixing the guide core relative to the catheter, which is fixedly connected with the catheter and is provided with a first locking portion and a second locking portion, both locked to the guide core in an unlockable manner respectively, and spaced apart from each other along an axial direction of the guide core;

wherein the guide core locking piece has a first locking position and a second locking position, wherein at the first locking position, the first locking portion is in an unlock condition, the guide core is locked by the second locking portion in front of the first locking portion, the stent conveying device sleeved on the guide core is slidden between the first locking portion and the second locking portion along the guide core; and at the second locking position, the guide core is locked by the first locking portion, the second locking portion is in an unlock condition, and the stent conveying device is moved forward through the second locking portion.

2. The system of claim 1, wherein the guide core comprises:

a guide wire hole, for enabling the body guide wire to pass through, and a control wire hole, formed around the guide wire hole, formed on a sidewall of the guide core and is extended along a same direction with the guide core, wherein an outer wall of the guide core is formed into a noncircular section structure in profiled connection with the stent conveying device, and the noncircular section structure is provided with a convex form, forming the control wire hole.

3. The system of claim 1, wherein the system is used for implanting the membrane and the stent at a three-branch vessel of an aortic arch.

* * * * *